US012558030B2

(12) United States Patent
Zott et al.

(10) Patent No.: US 12,558,030 B2
(45) Date of Patent: *Feb. 24, 2026

(54) DEVICE FOR DETECTING AND ILLUMINATING THE VASCULATURE USING AN FPGA

(71) Applicant: AccuVein Inc., Medford, NY (US)

(72) Inventors: Joseph Zott, Menlo Park, CA (US); Fred Wood, Medford, NY (US); Dmitriy Yavid, Stony Brook, NY (US); Seung P. Kim, San Francisco, CA (US); Klaus Zietlow, Piedmont, CA (US)

(73) Assignee: AccuVein Inc., Medford, NY (US)

( * ) Notice: Subject to any disclaimer, the term of this patent is extended or adjusted under 35 U.S.C. 154(b) by 201 days.

This patent is subject to a terminal disclaimer.

(21) Appl. No.: 17/991,924

(22) Filed: Nov. 22, 2022

(65) Prior Publication Data

US 2023/0136639 A1     May 4, 2023

Related U.S. Application Data

(63) Continuation of application No. 16/789,459, filed on Feb. 13, 2020, now Pat. No. 11,510,617, which is a (Continued)

(51) Int. Cl.
*A61B 5/00* (2006.01)
*A61B 90/00* (2016.01)
(Continued)

(52) U.S. Cl.
CPC ............ *A61B 5/489* (2013.01); *A61B 5/0033* (2013.01); *A61B 5/0062* (2013.01);
(Continued)

(58) Field of Classification Search
None
See application file for complete search history.

(56) References Cited

U.S. PATENT DOCUMENTS 3,136,310 A     6/1964   Meltzer
3,349,762 A   10/1967   Kapany
(Continued)

FOREIGN PATENT DOCUMENTS

FR          2289149          5/1976
GB          1298707         12/1972
(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.

(Continued)

*Primary Examiner* — Christopher Koharski
*Assistant Examiner* — Farouk A Bruce
(74) *Attorney, Agent, or Firm* — Thomas A. O'Rourke; James Bongiorno; O'Rourke IP Law, PLLC

(57) ABSTRACT
A laser based vascular illumination system utilizing a FPGA for detecting vascular positions, processing an image of such vasculature positions, and projecting the image thereof onto the body of a patient.

4 Claims, 8 Drawing Sheets

Related U.S. Application Data continuation of application No. 15/679,277, filed on Aug. 17, 2017, now Pat. No. 10,568,518, which is a continuation of application No. 14/723,674, filed on May 28, 2015, now Pat. No. 9,782,079, which is a continuation of application No. 13/957,767, filed on Aug. 2, 2013, now Pat. No. 9,072,426.

(60) Provisional application No. 61/678,726, filed on Aug. 2, 2012.

(51) Int. Cl.
    *A61M 5/42*              (2006.01)
    *G02B 26/10*             (2006.01)
(52) U.S. Cl.
    CPC ............ *A61B 5/0082* (2013.01); *A61B 5/743* (2013.01); *A61B 2090/366* (2016.02); *A61M 5/427* (2013.01); *G02B 26/101* (2013.01)

(56) References Cited

U.S. PATENT DOCUMENTS

| | | | |
|---|---|---|---|
| 3,511,227 | A | 5/1970 | Johnson |
| 3,527,932 | A | 9/1970 | Thomas |
| 3,818,129 | A | 6/1974 | Yamamoto |
| 3,984,629 | A | 10/1976 | Gorog |
| 4,030,209 | A | 6/1977 | Dreiding |
| 4,057,784 | A | 11/1977 | Tafoya |
| 4,109,647 | A | 8/1978 | Stern et al. |
| 4,162,405 | A | 7/1979 | Chance et al. |
| 4,182,322 | A | 1/1980 | Miller |
| 4,185,808 | A | 1/1980 | Donohoe et al. |
| 4,213,678 | A | 7/1980 | Pomerantzeff et al. |
| 4,265,227 | A | 5/1981 | Ruge |
| 4,312,357 | A | 1/1982 | Andersson et al. |
| 4,315,318 | A | 2/1982 | Kato et al. |
| 4,321,930 | A | 3/1982 | Jobsis et al. |
| 4,393,366 | A | 7/1983 | Hill |
| 4,495,949 | A | 1/1985 | Stoller |
| 4,502,075 | A | 2/1985 | DeForest et al. |
| 4,510,938 | A | 4/1985 | Jobsis et al. |
| 4,536,790 | A | 8/1985 | Kruger et al. |
| 4,565,968 | A | 1/1986 | Macovski |
| 4,567,896 | A | 2/1986 | Barnea et al. |
| 4,576,175 | A | 3/1986 | Epstein |
| 4,586,190 | A | 4/1986 | Tsuji |
| 4,590,948 | A | 5/1986 | Nilsson |
| 4,596,254 | A | 6/1986 | Adrian et al. |
| 4,619,249 | A | 10/1986 | Landry |
| 4,669,467 | A | 6/1987 | Willett et al. |
| 4,697,147 | A | 9/1987 | Moran et al. |
| 4,699,149 | A | 10/1987 | Rice |
| 4,703,758 | A | 11/1987 | Omura |
| 4,766,299 | A | 8/1988 | Tierney et al. |
| 4,771,308 | A | 9/1988 | Tejima et al. |
| 4,780,919 | A | 11/1988 | Harrison |
| 4,799,103 | A | 1/1989 | Muckerheide |
| 4,817,622 | A | 4/1989 | Pennypacker et al. |
| 4,846,183 | A | 7/1989 | Martin |
| 4,861,973 | A | 8/1989 | Hellekson et al. |
| 4,862,894 | A | 9/1989 | Fujii |
| 4,899,756 | A | 2/1990 | Sonek |
| 4,901,019 | A | 2/1990 | Wedeen |
| 4,926,867 | A | 5/1990 | Kanda et al. |
| RE33,234 | E | 6/1990 | Landry |
| 4,938,205 | A | 7/1990 | Nudelman |
| 5,074,642 | A | 12/1991 | Hicks |
| 5,088,493 | A | 2/1992 | Giannini et al. |
| 5,103,497 | A | 4/1992 | Hicks |
| 5,146,923 | A | 9/1992 | Dhawan |
| 5,174,298 | A | 12/1992 | Dolfi et al. |
| 5,184,188 | A | 2/1993 | Bull et al. |
| 5,214,458 | A | 5/1993 | Kanai |
| 5,222,495 | A | 6/1993 | Clarke et al. |
| 5,261,581 | A | 11/1993 | Harden, Sr. |
| 5,293,873 | A | 3/1994 | Fang |
| 5,339,817 | A | 8/1994 | Nilsson |
| 5,371,347 | A | 12/1994 | Plesko |
| 5,406,070 | A | 4/1995 | Edgar et al. |
| 5,418,546 | A | 5/1995 | Nakagakiuchi et al. |
| 5,423,091 | A | 6/1995 | Lange |
| 5,436,655 | A | 7/1995 | Hiyama et al. |
| 5,445,157 | A | 8/1995 | Adachi et al. |
| D362,910 | S | 10/1995 | Creaghan |
| 5,485,530 | A | 1/1996 | Lakowicz et al. |
| 5,487,740 | A | 1/1996 | Sulek et al. |
| 5,494,032 | A | 2/1996 | Robinson et al. |
| 5,497,769 | A | 3/1996 | Gratton et al. |
| 5,501,680 | A | 3/1996 | Kurtz |
| 5,504,316 | A | 4/1996 | Bridgelall et al. |
| 5,519,208 | A | 5/1996 | Esparza et al. |
| 5,541,820 | A | 7/1996 | McLaughlin |
| 5,542,421 | A | 8/1996 | Erdman |
| 5,598,842 | A | 2/1997 | Ishihara et al. |
| 5,603,328 | A | 2/1997 | Zucker et al. |
| 5,608,210 | A | 3/1997 | Esparza et al. |
| 5,610,387 | A | 3/1997 | Bard et al. |
| 5,625,458 | A | 4/1997 | Alfano et al. |
| 5,631,976 | A | 5/1997 | Bolle et al. |
| 5,655,530 | A | 8/1997 | Messerschmidt |
| 5,678,555 | A | 10/1997 | O'Connell |
| 5,716,796 | A | 2/1998 | Bull et al. |
| 5,719,399 | A | 2/1998 | Alfano et al. |
| 5,740,801 | A | 4/1998 | Branson |
| 5,747,789 | A | 5/1998 | Godik |
| 5,756,981 | A | 5/1998 | Roustaei et al. |
| 5,758,650 | A | 6/1998 | Miller et al. |
| 5,772,593 | A | 6/1998 | Hakamata |
| 5,787,185 | A | 7/1998 | Clayden |
| 5,814,040 | A | 9/1998 | Nelson et al. |
| 5,836,877 | A | 11/1998 | Zavislan |
| 5,847,394 | A | 12/1998 | Alfano et al. |
| 5,860,967 | A | 1/1999 | Zavislan et al. |
| 5,865,828 | A | 2/1999 | Jeng |
| 5,929,443 | A | 7/1999 | Alfano et al. |
| 5,946,220 | A | 8/1999 | Lemelson |
| 5,947,906 | A | 9/1999 | Dawson, Jr. et al. |
| 5,966,204 | A | 10/1999 | Abe |
| 5,966,230 | A | 10/1999 | Swartz et al. |
| 5,969,754 | A | 10/1999 | Zeman |
| 5,982,553 | A | 11/1999 | Bloom et al. |
| 5,988,817 | A | 11/1999 | Mizushima et al. |
| 5,995,856 | A | 11/1999 | Mannheimer et al. |
| 5,995,866 | A | 11/1999 | Lemelson |
| 6,006,126 | A | 12/1999 | Cosman |
| 6,032,070 | A | 2/2000 | Flock et al. |
| 6,056,692 | A | 5/2000 | Schwartz |
| 6,061,583 | A | 5/2000 | Ishihara et al. |
| 6,083,486 | A | 7/2000 | Weissleder et al. |
| 6,101,036 | A | 8/2000 | Bloom |
| 6,113,536 | A | 9/2000 | Aboul-Hosn et al. |
| 6,122,042 | A | 9/2000 | Wunderman et al. |
| 6,132,379 | A | 10/2000 | Patacsil et al. |
| 6,135,599 | A | 10/2000 | Fang |
| 6,141,985 | A | 11/2000 | Cluzeau et al. |
| 6,142,650 | A | 11/2000 | Brown et al. |
| 6,149,061 | A | 11/2000 | Massieu et al. |
| 6,149,644 | A | 11/2000 | Xie |
| 6,171,301 | B1 | 1/2001 | Nelson et al. |
| 6,178,340 | B1 | 1/2001 | Svetliza |
| 6,179,260 | B1 | 1/2001 | Ohanian |
| 6,230,046 | B1 | 5/2001 | Crane et al. |
| 6,240,309 | B1 | 5/2001 | Yamashita et al. |
| 6,251,073 | B1 | 6/2001 | Imran et al. |
| 6,263,227 | B1 | 7/2001 | Boggett et al. |
| 6,272,376 | B1 | 8/2001 | Marcu et al. |
| 6,301,375 | B1 | 10/2001 | Choi |
| 6,305,804 | B1 | 10/2001 | Rice et al. |
| 6,314,311 | B1 | 11/2001 | Williams et al. |
| 6,334,850 | B1 | 1/2002 | Amano et al. |
| 6,353,753 | B1 | 3/2002 | Flock et al. |
| 6,424,858 | B1 | 7/2002 | Williams |
| 6,436,655 | B1 | 8/2002 | Bull et al. |

(56) References Cited

U.S. PATENT DOCUMENTS

| | | | |
|---|---|---|---|
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl et al. |
| 6,542,246 B1 | 4/2003 | Toida |
| 6,556,854 B1 | 4/2003 | Sato et al. |
| 6,556,858 B1 | 4/2003 | Zeman |
| 6,599,247 B1 | 7/2003 | Stetten |
| 6,631,286 B2 | 10/2003 | Pfeiffer et al. |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer et al. |
| 6,777,199 B2 | 8/2004 | Bull et al. |
| 6,782,161 B2 | 8/2004 | Barolet et al. |
| 6,845,190 B1 | 1/2005 | Smithwick et al. |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan, Jr. |
| 6,971,579 B2 | 12/2005 | Barkan |
| 6,980,852 B2 | 12/2005 | Jersey-Willuhn et al. |
| 7,092,087 B2 | 8/2006 | Kumar et al. |
| 7,113,817 B1 | 9/2006 | Winchester, Jr. et al. |
| 7,158,660 B2 | 1/2007 | Gee, Jr. et al. |
| 7,158,859 B2 | 1/2007 | Wang et al. |
| 7,204,424 B2 | 4/2007 | Yavid et al. |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,280,860 B2 | 10/2007 | Ikeda et al. |
| 7,283,181 B2 | 10/2007 | Allen et al. |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts et al. |
| 7,428,997 B2 | 9/2008 | Wiklof et al. |
| 7,431,695 B1 | 10/2008 | Creaghan |
| 7,448,995 B2 | 11/2008 | Wiklof et al. |
| 7,532,746 B2 | 5/2009 | Marcotte et al. |
| 7,545,837 B2 | 6/2009 | Oka |
| 7,559,895 B2 | 7/2009 | Stetten et al. |
| 7,579,592 B2 | 8/2009 | Kaushal |
| 7,608,057 B2 | 10/2009 | Woehr et al. |
| 7,699,776 B2 | 4/2010 | Walker et al. |
| 7,708,695 B2 | 5/2010 | Akkermans et al. |
| 7,791,561 B2 | 9/2010 | Hajjar |
| 7,792,334 B2 | 9/2010 | Cohen et al. |
| 7,846,103 B2 | 12/2010 | Cannon, Jr. et al. |
| 7,848,103 B2 | 12/2010 | Zhan |
| 7,904,138 B2 | 3/2011 | Goldman et al. |
| 7,904,139 B2 | 3/2011 | Chance |
| 7,925,332 B2 | 4/2011 | Crane et al. |
| 7,966,051 B2 | 6/2011 | Xie et al. |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Boccoleri et al. |
| 8,364,246 B2 | 1/2013 | Thierman |
| 8,467,855 B2 | 6/2013 | Yasui |
| 8,480,662 B2 | 7/2013 | Stolen et al. |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,537,203 B2 | 9/2013 | Seibel et al. |
| 8,548,572 B2 | 10/2013 | Crane |
| 8,630,465 B2 | 1/2014 | Wieringa et al. |
| 8,649,848 B2 | 2/2014 | Crane et al. |

| | | | |
|---|---|---|---|
| 2001/0006426 A1 | 7/2001 | Son et al. |
| 2001/0056237 A1 | 12/2001 | Cane et al. |
| 2002/0016533 A1 | 2/2002 | Marchitto et al. |
| 2002/0118338 A1 | 8/2002 | Kohayakawa |
| 2002/0188203 A1 | 12/2002 | Smith et al. |
| 2003/0018271 A1 | 1/2003 | Kimble |
| 2003/0037375 A1 | 2/2003 | Riley et al. |
| 2003/0047683 A1 | 3/2003 | Kaushal |
| 2003/0052105 A1 | 3/2003 | Nagano et al. |
| 2003/0120154 A1 | 6/2003 | Sauer et al. |
| 2003/0125629 A1 | 7/2003 | Ustuner |
| 2003/0156260 A1 | 8/2003 | Putilin et al. |
| 2003/0210810 A1 | 11/2003 | Gee |
| 2004/0015062 A1 | 1/2004 | Ntziachristos et al. |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0171923 A1 | 9/2004 | Kalafut et al. |
| 2004/0222301 A1 | 11/2004 | Willins et al. |
| 2004/0237051 A1 | 11/2004 | Clauson |
| 2005/0003323 A1 | 1/2005 | Katsuda |
| 2005/0017924 A1 | 1/2005 | Utt et al. |
| 2005/0023356 A1 | 2/2005 | Wiklof |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085732 A1 | 4/2005 | Sevick-Muraca et al. |
| 2005/0085802 A1 | 4/2005 | Gruzdev et al. |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner et al. |
| 2005/0154303 A1 | 7/2005 | Walker et al. |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov et al. |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0013473 A1* | 1/2006 | Woodfill ................ G01C 11/06 |
| | | 382/154 |
| 2006/0020212 A1 | 1/2006 | Xu et al. |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle et al. |
| 2006/0103811 A1 | 5/2006 | May et al. |
| 2006/0122515 A1 | 6/2006 | Zeman et al. |
| 2006/0129037 A1 | 6/2006 | Kaufman et al. |
| 2006/0129038 A1 | 6/2006 | Zelenchuk et al. |
| 2006/0151449 A1 | 7/2006 | Warner, Jr. et al. |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0247514 A1 | 11/2006 | Panasyuk |
| 2006/0253010 A1 | 11/2006 | Brady et al. |
| 2006/0271028 A1 | 11/2006 | Altshuler et al. |
| 2006/0276712 A1 | 12/2006 | Stothers |
| 2007/0015980 A1 | 1/2007 | Numada et al. |
| 2007/0016079 A1 | 1/2007 | Freeman et al. |
| 2007/0070302 A1 | 3/2007 | Govorkov et al. |
| 2007/0115435 A1 | 5/2007 | Rosendaal |
| 2007/0129634 A1 | 6/2007 | Hickey et al. |
| 2007/0162094 A1* | 7/2007 | Goldman ............. A61B 5/0037 |
| | | 607/89 |
| 2007/0176851 A1 | 8/2007 | Willey et al. |
| 2007/0225582 A1 | 9/2007 | Diab |
| 2007/0238957 A1 | 10/2007 | Yared |
| 2008/0039701 A1 | 2/2008 | Ali |
| 2008/0045841 A1 | 2/2008 | Wood et al. |
| 2008/0147147 A1 | 6/2008 | Griffiths et al. |
| 2008/0194930 A1 | 8/2008 | Harris et al. |

(56)          References Cited

U.S. PATENT DOCUMENTS

| | | |
|---|---|---|
| 2008/0214940 A1 | 9/2008 | Benaron |
| 2009/0018414 A1 | 1/2009 | Toofan |
| 2009/0028461 A1 | 1/2009 | Wieringa |
| 2009/0082629 A1 | 3/2009 | Dotan |
| 2009/0171205 A1 | 7/2009 | Kharin et al. |
| 2010/0020078 A1 | 1/2010 | Shpunt |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2011/0275932 A1 | 11/2011 | Leblond et al. |
| 2013/0147916 A1 | 6/2013 | Bennett et al. |
| 2014/0039309 A1 | 2/2014 | Harris et al. |
| 2014/0046291 A1 | 2/2014 | Harris et al. |
| 2014/0194747 A1 | 7/2014 | Kruglick |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08-023501 A | 1/1996 |
| JP | 08-164123 | 6/1996 |
| JP | 2000-316866 A | 11/2000 |
| JP | 2002-328428 A | 11/2002 |
| JP | 2002-345953 A | 12/2002 |
| JP | 2004-237051 | 8/2004 |
| JP | 2004-329786 A | 11/2004 |
| KR | 2003-0020152 A | 3/2003 |
| WO | WO 1994 22370 | 10/1994 |
| WO | WO 1996 39925 | 12/1996 |
| WO | WO 1998 26583 | 6/1998 |
| WO | WO 1999 48420 | 9/1999 |
| WO | WO 2001-82786 | 11/2001 |
| WO | WO 2003-009750 | 2/2003 |
| WO | WO 2005-053773 | 6/2005 |
| WO | WO 2007-078447 | 7/2007 |

OTHER PUBLICATIONS

Nikbin, Darius, "IPMS Targets Colour Laser Projectors," Optics & Laser Europe, Mar. 10, 2006, Isue 137, p. 11.
Http://sciencegeekgirl.wordpress.com/category/science-myths/page/2/ Myth 7: Blood is Blue.
Http://www.exploratorium.edu/sports/hnds_up/hands6.html "Hands Up! To Do & Notice: Getting the Feel of Your Hand".
Http://www.wikihow.com/See-Blook-Veins-in-Your-Hand-With-a-Flashlight "How to See Blood Veins in Your Hand With a Flashlight".

* cited by examiner

Vein Algo Architecture

2-D Moving Window Sum Generator

Latency = X-Sum Buffer Size + Y-Sum Buffer Size

X-Sum Buffer Size = (boxsize - 1)*(number_of_horizontal_pixels) ;
Y-Sum Buffer Size = (boxsize - 1);

X-sum generator (Boxsize – 1) stage shift register

DEVICE FOR DETECTING AND ILLUMINATING THE VASCULATURE USING AN FPGA

CROSS REFERENCE TO RELATED APPLICATIONS

This application is a continuation of U.S. patent application Ser. No. 16/789,459, filed on Feb. 13, 2020, which is a continuation of U.S. patent application Ser. No. 15/679,277, filed on Aug. 17, 2017, now issued as U.S. Pat. No. 10,568,518, which is a continuation of U.S. patent application Ser. No. 14/723,674, filed on May 28, 2015, now issued as U.S. Pat. No. 9,782,079, which is a continuation of U.S. patent application Ser. No. 13/957,767, filed on Aug. 2, 2013, now issued as U.S. Pat. No. 9,072,426, which claims priority on U.S. Provisional Patent Application Ser. No. 61/678,726, filed on Aug. 2, 2012, with the disclosures of each being incorporated herein by reference.

BACKGROUND

Summary

A laser based vascular illumination system utilizing a FPGA for detecting vascular positions, processing an image of such vasculature positions, and projecting the image thereof onto the body of a patient.

BRIEF DESCRIPTION

FIG. 1 Block diagram of a system for detecting and illuminating the vasculature in a patient.

Figure 2:
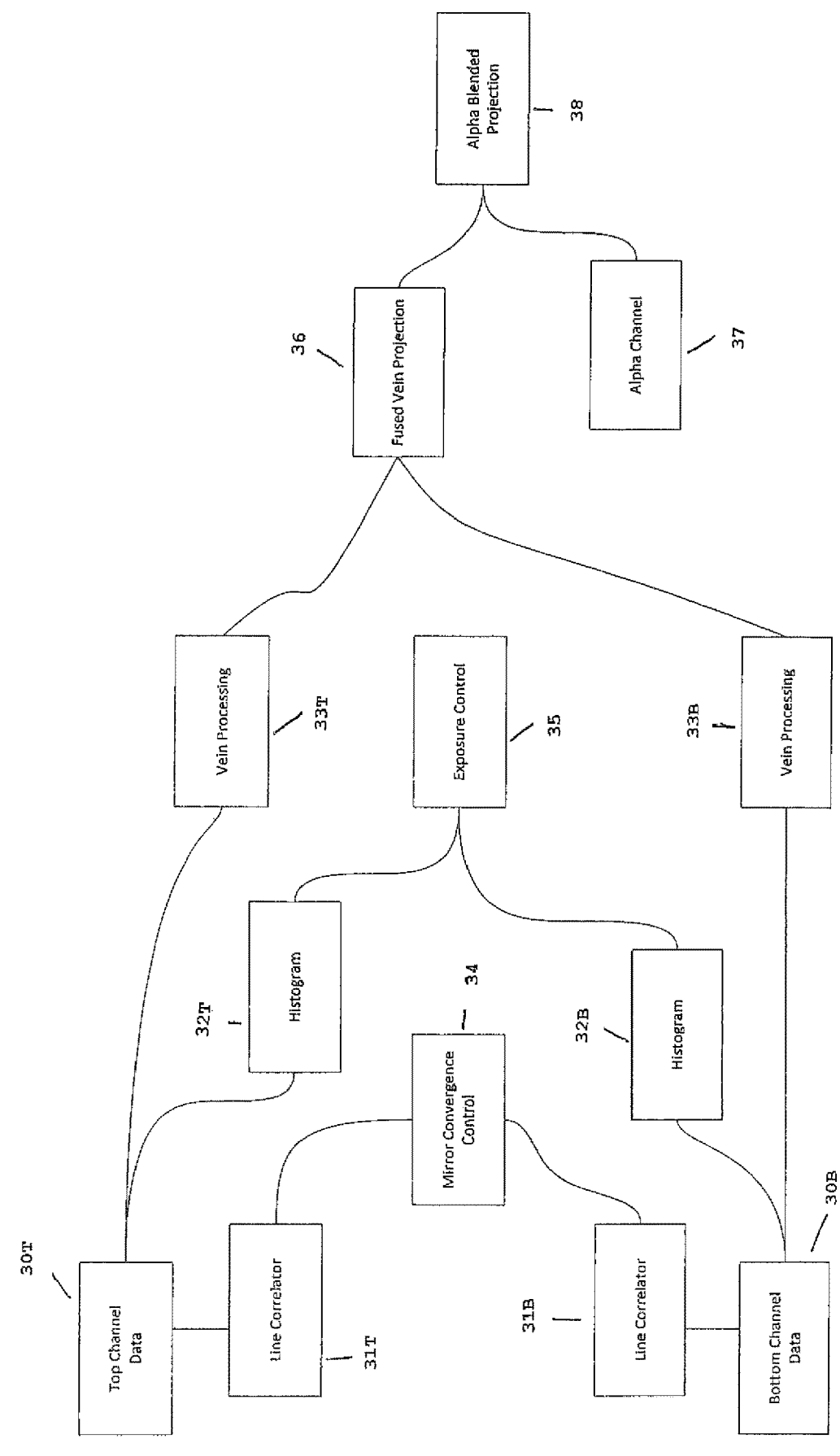
FIG. 2 Shows the signal processing flow of the FPGA.
Figure 7:
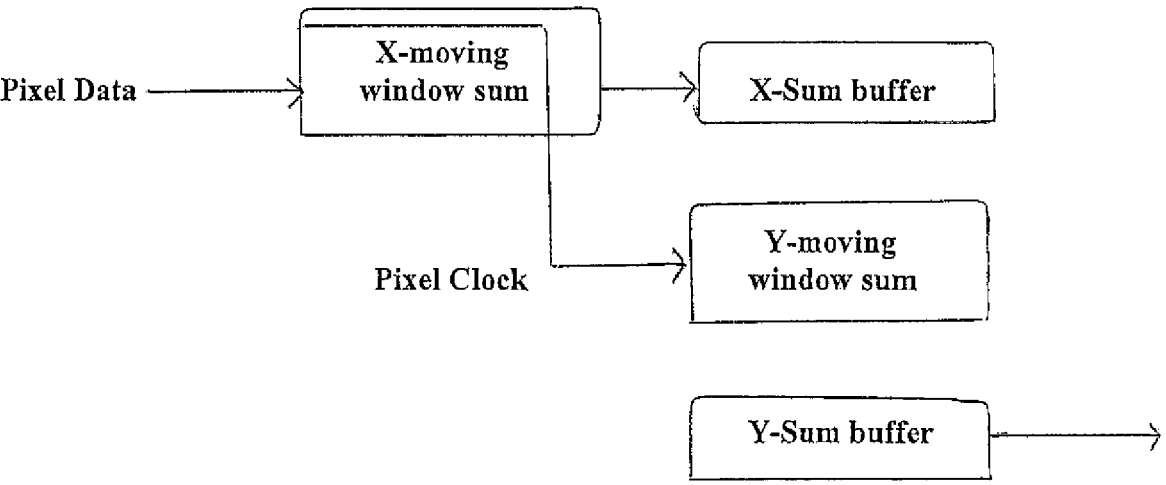

FIG. 7 2-D Moving Window Sum Generator.

Figure 8:
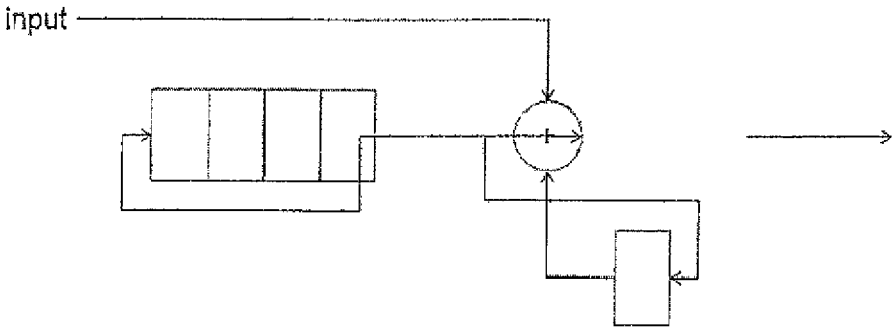

FIG. 8 shows a X-sum generator.

DETAILED DESCRIPTION

Figure 1:
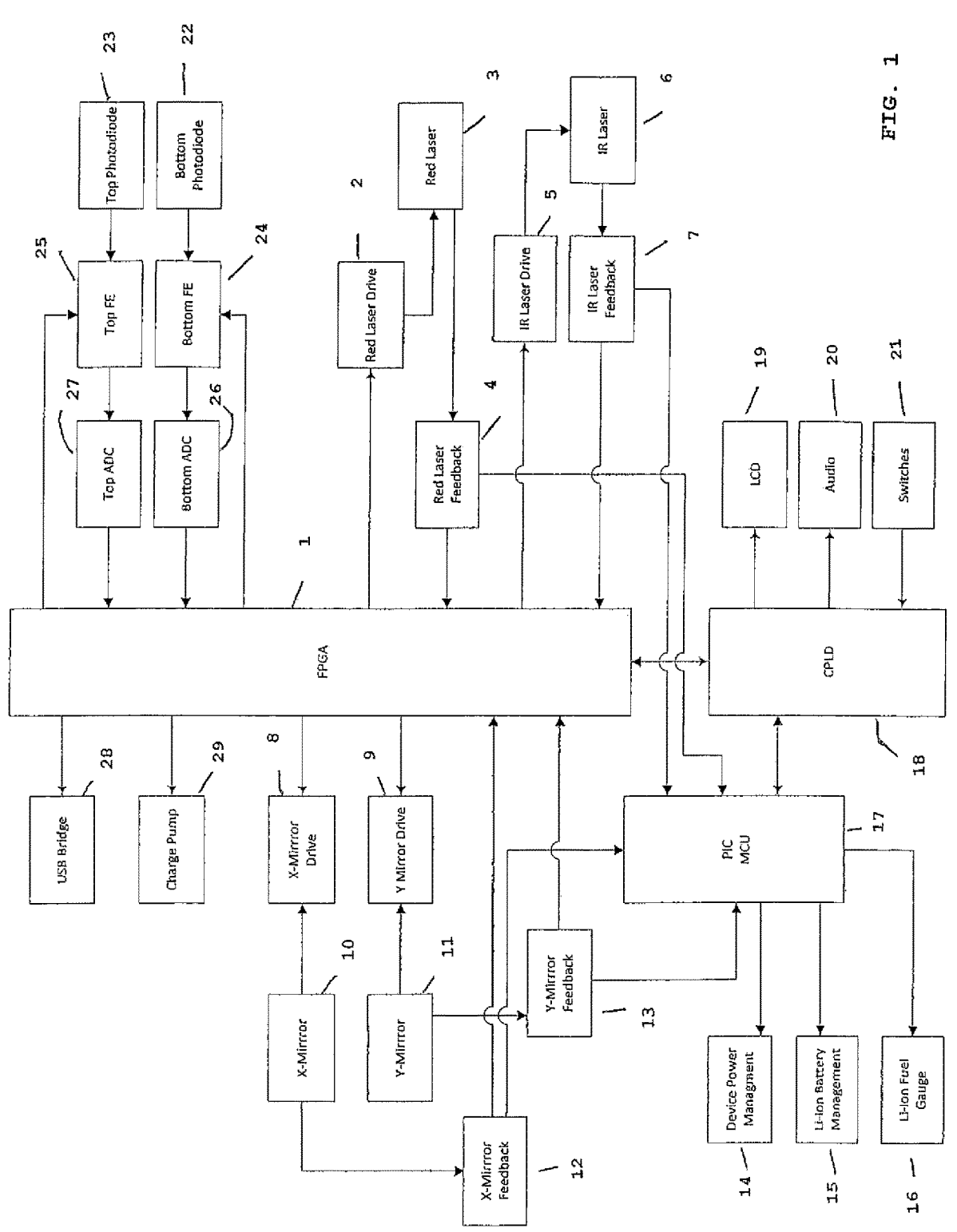

FIG. 1 shows a block diagram of a system for detecting and illuminating the vasculature in a patient The system shown in the block diagram of FIG. 1 is used for detecting the location of veins on a patient and illuminating the veins.

The disclosures of U.S. patent application Ser. No. 12/804,506, now issued as U.S. Pat. No. 8,463,364 are incorporated herein by reference.

In a preferred embodiment, FIGS. 30-47 of application Ser. No. 12/804,506 illustrates an assembly of a housing that may be used in the present invention. In the present invention, circuit boards 43, 44 and 15 of application Ser. No. 12/804,506 may be modified to contain the circuitry described by the block diagram in FIG. 1. The remainder of the device in FIGS. 30-47 can remain substantially the same.

In FIG. 1 an FPGA 1 (field programmable gate array) is configured to control a red laser drive 2 which in turn drives a red laser 3. The output of the red laser 3 is controlled in a manner so as to illuminate the detected veins. A red laser feedback 4 detects the output of the red laser 3 and sends the information to the FPGA 1. Accordingly, a closed loop is formed whereby the FPGA 1 can both drive the Red laser 3 and receive feedback as to the red laser 3 state.

FPGA 1 outputs data to an IR laser drive 5 which in turn drives an IR laser 6. The output of the IR laser 6 is controlled to output an intensity of IR light, aimed at the area of the body where veins are located, sufficient to detect the veins. An IR laser feedback 7 detects the output of the IR laser 6 and sends the information to the FPGA 1. Accordingly, a closed loop is formed whereby the FPGA 1 can both drive the IR Laser 6 and receive feedback as to the IR laser 6 state.

FPGA 1 communicates to both a x-mirror drive 8 and a y-mirror drive 9 to drive x-mirror 10 and y-mirror 11 in such a manner that a raster pattern is formed on the patient when the Red laser 3 and the IR laser 6 are coaxially projected thereon. X-mirror feedback 12 and y-mirror feedback 13 detect the positions of the x-mirror 10 and y-mirror 11, respectively, and communicates such information to the FPGA1.

Top photodiode 23 and bottom photodiode 22 receive the IR Laser 6 reflected off the patient, converts the light into an analog signal which is provided to Top FE 25 and Bottom FE 24, and then to Top ADC 27 and bottom ADC 25, respectively. The top FE 25 and the bottom FE 24 are front end circuits that provide analog filtering, gain control and threshold of the analog signals. The Top ADC 27 and bottom ADC 26 are analog to digital converters that convert the analog signals to digital representations thereof to be communicated to the FPGA 1. Control lines are provided from the FPGA 1 to the top FE 25 and the bottom FE 24 to set parameters such as, for example, gain control and analog filtering.

From a mechanical standpoint, the red laser 3 and the IR laser 6 are co axially aligned and projected off of mirrors X-mirror 10 and Y-mirror 11 to form a pattern, such as for example, a raster pattern on the patient. The IR laser 6 reflects off the patient and is received by top photodiode 23 and photodiode 22. The reflected IR light contains information as to the location of the veins (IR light is absorbed by the blood in the veins and therefore the amount or reflected IR light is lower when the IR laser 6 is aimed at a vein. The FPGA 1 time sequentially receives in the signal form the top ADC 27 and the bottom ADC and can form two partial and/or full frame images of the reflected IR light (hereinafter a top channel data and a bottom channel data wherein the top channel data is received from the top ADC 27 and the bottom channel data is received from the bottom ADC). The FPGA 1 processes one or both of the partial and/or full image to detect and enhance the image of the veins. The enhanced image is time sequentially projected by the Red laser 3 onto the patient.

A CPLD is provided for controlling an LCD 19 with displays user information related to the operating status of the device. It also controls an audio 20 output to provide audible tones to the user. Finally the CPLD 18 controls the switches 21 on the unit for turning on and off the units as well as selecting user modes and entering data.

A microprocessor PIC MCU 17 is provided for receiving and monitoring the IR laser feedback 7 signal, the red laser feedback 4 signal, the x-mirror feedback 12 signal and the y-mirror feedback 13 signal. Since these signals are also provided to the FPGA 1, redundancy monitoring of the signals is provided by the PIC MCU 17. This is particularly important when regulatory requirements require redundant monitoring of the laser power and movement to comply with safety requirements. The NC MCU 17 also monitors the device power management 14, the Li-ion Battery management 15 circuitry and the Li-ion Fuel gauge 16.

FIG. 2 Shows an example of the signal processing flow of the FPGA

FIG. 2 shows an embodiment of the signal processing algorithm of the FPGA of FIG. 1. As described with reference to FIG. 1, the image of the reflected IR laser 6 is time sequentially stored in the FPGA 1 as top channel data 30T and bottom channel data 30B.

The X-mirror 10 oscillates about a single axis to move the laser beam from the IR laser 6 to form a line. The beam moves first in one direction and then back in the other direction. It is critical that the left to right image data be in convergence with the right to left data. The top line correlator 31T measures the shift in the convergence of the top channel data 30T and supplies the information to the mirror convergence control 34. Similarly, the bottom line correlator 31B measures the shift in the convergence of the bottom channel data 30B and supplies the information to the mirror convergence control 34. The mirror convergence control 34 can adjust the control signals provided from the FPGA 1 to the x-mirror drive 8 so as to converge the data.

A top histogram 32T receives the top channel data 30T and generates a histogram based upon an entire frame of the top channel data 30T. Similarly, a bottom histogram 32B receives the top channel data 30B and generates a histogram based upon an entire frame of the bottom channel data 30B. The histograms contain information describing the characteristics of the images, including but not limited to contrast and intensity levels. The top histogram 32T and the bottom histogram 32B are provided to exposure control 35. Exposure control 35 communicates appropriate signals the IR laser drive 5 to adjust the power of the IR laser 6 on a frame by frame basis until the histograms indicate appropriate images. The exposure control 35 also communicates with the top FE 25 and bottom FE 24 to adjust parameters such as setting thresholds and setting electrical gain.

A top vein processing 33T block receives the top channel data 30T and performs image processing to detect vein patterns and provides the enhanced vein image to fused vein projection 36. Similarly, bottom vein processing 33B block receives the bottom channel data 30B and performs image processing to detect vein patterns and provides the enhanced vein image to fused vein projection 36. The fused vein projection 36 forms a single image and communicates the Image to the alpha blended projection 38. The fused vein projection 36 can form the single image by merging the images from the top vein processing 33T and bottom vein processing 33B. Alternative, the fused vein projection 36 can simply select the best image received from the top vein processing 33T and the bottom vein processing 33B.

Alpha channel 37 forms an image that contains graphical data, such as text or characters. Alpha channel 37 and fused vein projection 36 are provided to alpha blended projection 38 with drives the IR laser drive 5 to display an image which is the combination of the fused vein projection 36 and the alpha channel 37.

Figure 3:
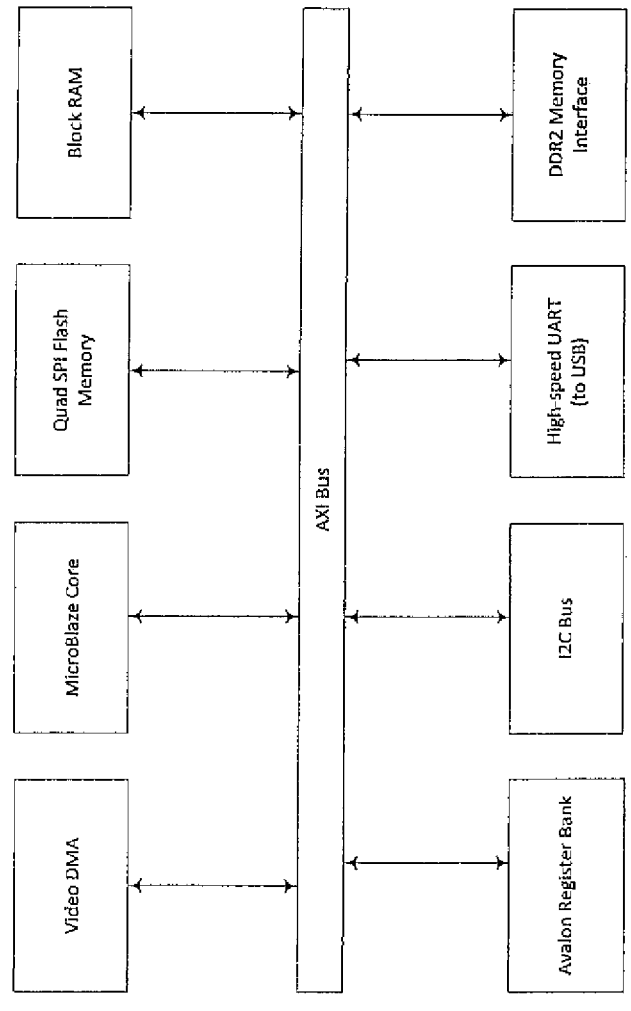
FIG. 3 shows the internal bus architecture of the FPGA.

FIG. 3 shows an example of the internal bus architecture of the FPGA

Figure 4:
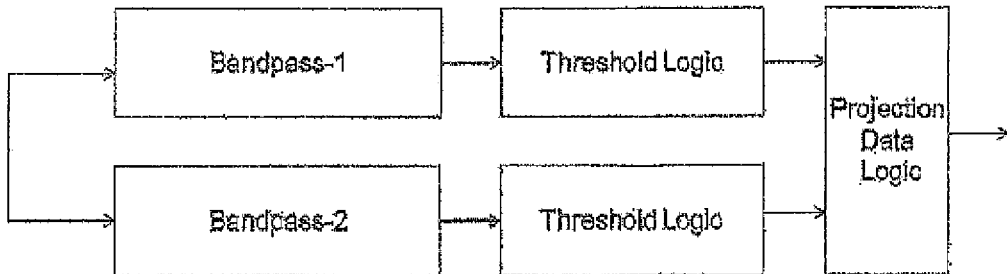
FIG. 4 shows details of the vein processing.

FIG. 4 shows details of the top vein processing 33T and bottom vein processing 33B.

Figure 5:
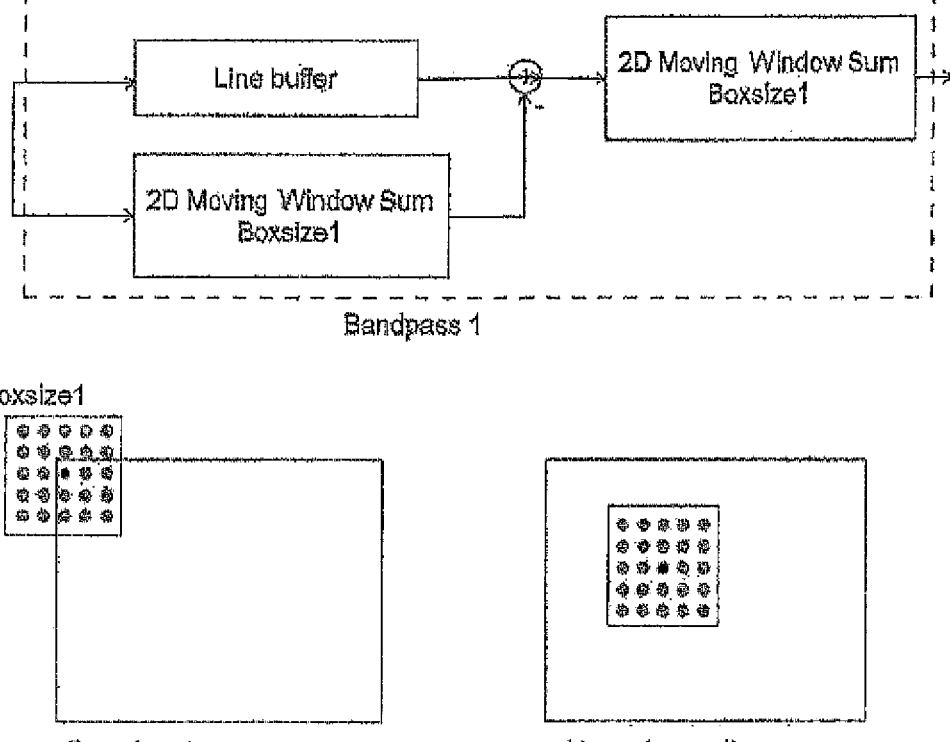
FIG. 5 shows the vein processing at the boundary of the image frames.

FIG. 5 shows the vein processing at the boundary of the image frames.

Figure 6:
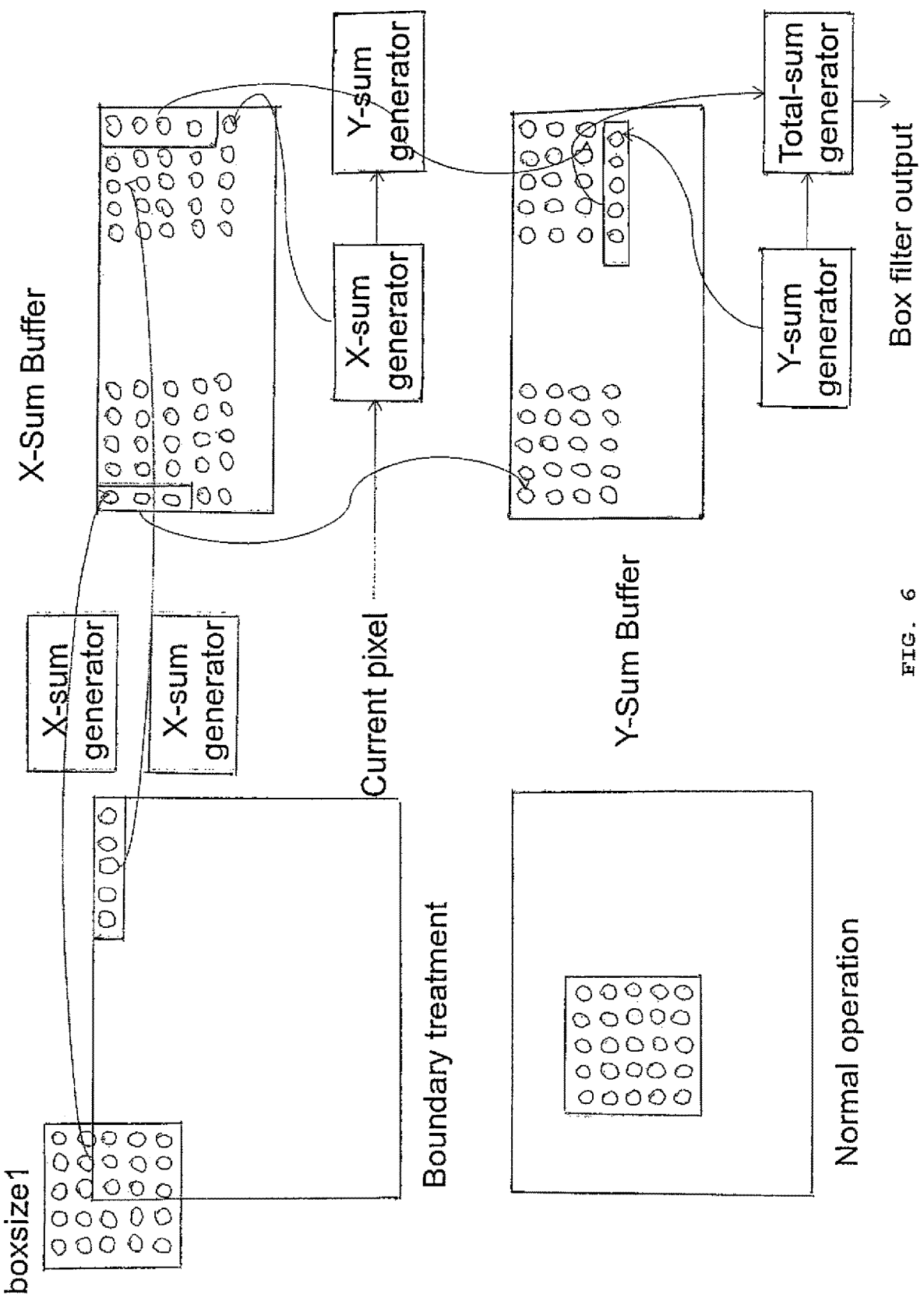
FIG. 6 shows further detail of the vein processing at the boundary of the image frames.

FIG. 6 shows further detail of the vein processing at the boundary of the image frames.

FIG. 7 shows the 2-D Moving Window Sum Generator.

FIG. 8 shows a X-sum generator.

What is claimed is:

1. A vein imaging device configured to obtain and project an image of subcutaneous veins onto a patient to overlie the imaged veins, said vein imaging device comprising:
   a first laser configured to emit a beam of light at an infrared wavelength;
   a second laser configured to emit a beam of light at a red wavelength;
   an x-mirror;
   an x-mirror driver;
   a y-mirror;
   a y-mirror driver;
   a field programmable gate array (FPGA), said FPGA configured to control said x-mirror driver and said y-mirror driver to control said first laser, said second laser, said x-mirror and said y-mirror to selectively scan each of said beam of light at said infrared wavelength and said beam of light at said red wavelength onto the patient in a first and a second direction, to form respective lines in said first and second directions, and to scan said lines in a third direction and a fourth direction to thereby form a pattern of said infrared wavelength of light;
   wherein said FPGA is further configured to receive feedback of a state of said first laser and a state of said second laser, to form a closed loop to control an output of said first laser and an output of said second laser;
   a photodiode configured to receive a vein image formed from said scanned pattern of said infrared wavelength of light, and further configured to convert the received vein image into an analog signal;
   a front end circuit, said front end circuit configured to provide analog filtering, and gain control of the analog signal;
   an analog to digital converter (ADC), said ADC configured to convert the analog signal to a digital signal;
   wherein said FPGA is further configured to receive the digital signal and to perform normal vein image processing of an image frame of said received vein image, said normal vein image processing comprising:
   said FPGA being configured to collect pixel data from said photodiode, to perform an X-direction sum of pixel data for a plurality of boundary windows comprising a five by five matrix of pixels and to place said X-direction sum into an X-sum buffer, to perform a Y-direction sum of pixel data for said plurality of boundary windows, and to place said Y-direction sum into a Y-sum buffer, and to use a total sum generator to obtain a box filter output for each of said plurality of windows being the X-sum buffer added to the Y-sum buffer;
   wherein said FPGA is further configured to control said x-mirror driver and said y-mirror driver to control said first laser, said second laser, said x-mirror and said y-mirror to scan said red wavelength within said beam for projection of said processed vein image onto the patient; and
   wherein said FPGA is further configured to control said front end circuit to set said analog filtering and gain.

2. The imaging device according to claim 1, wherein said FPGA is further configured for boundary image processing, wherein a portion of one or more of said plurality of boundary windows extends beyond said image frame.

3. The imaging device according to claim 2, further comprising a pixel clock configured to time sequentially store said image in said FPGA.

4. The imaging device according to claim 3, further comprising:
    a pixel clock.

\* \* \* \* \*